219-121
5/5/81

SR
XR    4,265,747

United States Patent [19]
Copa et al.

[11]  4,265,747
[45]  May 5, 1981

[54] DISINFECTION AND PURIFICATION OF FLUIDS USING FOCUSED LASER RADIATION

[75] Inventors: William M. Copa, Wausau; Wayne B. Gitchel, Rothschild, both of Wis.

[73] Assignee: Sterling Drug Inc., New York, N.Y.

[21] Appl. No.: 41,526

[22] Filed: May 22, 1979

[51] Int. Cl.³ .............................. C02F 1/32; C02F 1/78
[52] U.S. Cl. ........................ 210/758; 204/DIG. 11; 210/760; 210/764; 219/121 LM; 422/23; 422/24; 422/29
[58] Field of Search ............... 204/DIG. 11; 210/18, 210/50, 60, 63 R, 63 Z, 64, 150, 151, 192, 194, 198 R, 205; 219/121 LM; 331/DIG. 1; 422/22–24, 29, 32

[56] References Cited

U.S. PATENT DOCUMENTS

| | | | |
|---|---|---|---|
| 2,271,895 | 2/1942 | Hartman | 204/176 |
| 3,405,045 | 10/1968 | Hoskins | 204/159.11 |
| 3,458,140 | 7/1969 | Schryver | 210/64 |
| 3,659,096 | 4/1972 | Kompanek | 250/43 |
| 3,794,299 | 2/1974 | Wagner et al. | 210/198 R |
| 3,843,521 | 10/1974 | Zeff | 422/24 |
| 3,914,173 | 10/1975 | Call et al. | 210/63 R |
| 3,941,670 | 3/1976 | Pratt, Jr. | 422/22 |
| 4,012,321 | 3/1977 | Koubek | 210/63 R |
| 4,028,246 | 6/1977 | Lund et al. | 210/151 |
| 4,042,325 | 8/1977 | Tensmeyer | 422/22 |

FOREIGN PATENT DOCUMENTS 2636094  2/1978  Fed. Rep. of Germany ............ 210/64

OTHER PUBLICATIONS

Parker, "Laser Radiation Reduces Coliform Counts in Water", *Water & Sewage Works*, vol. 123, May 1976, pp. 52 & 53.

Godwin, "Experiments with Laser Plasmas", *Plenum Press*, New York, 1974, pp. 691–711.

Prengle et al., "Ozone/UV Process Effective Wastewater Treatment", *Hydrocarbon Processing*, Oct. 1975, pp. 82–87.

Pratt, "Effect of Infrared Laser Radiation on Biological Systems", Biomed Phys. Biomater Sci. Lect., MIT, 1971, pp. 301–320.

*Primary Examiner*—Peter A. Hruskoci
*Attorney, Agent, or Firm*—Thomas L. Johnson; Allen H. Erickson; B. Woodrow Wyatt

[57]  ABSTRACT

Disinfection of aqueous media contaminated with microorganisms is effected by contacting said media with a gas phase in which a plasma is generated by focused laser radiation. Similarly, wastewaters containing organic susbstances are purified by contacting them with an oxygen-containing gas phase in which a plasma is generated by focused laser radiation which promotes oxidation of the organic substances to innocuous products.

17 Claims, 4 Drawing Figures

FIG. 1.
FIG. 2.
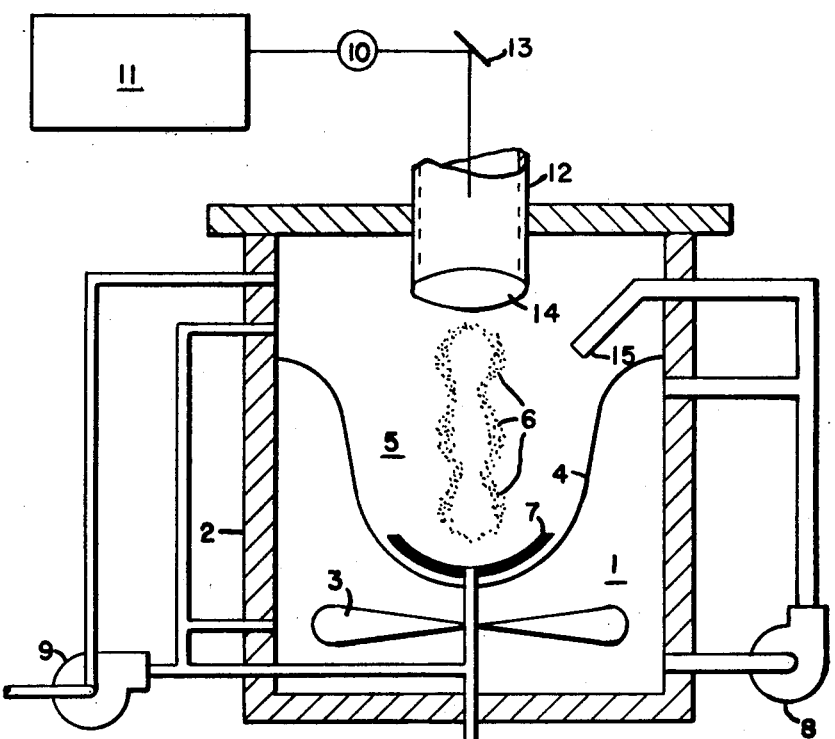
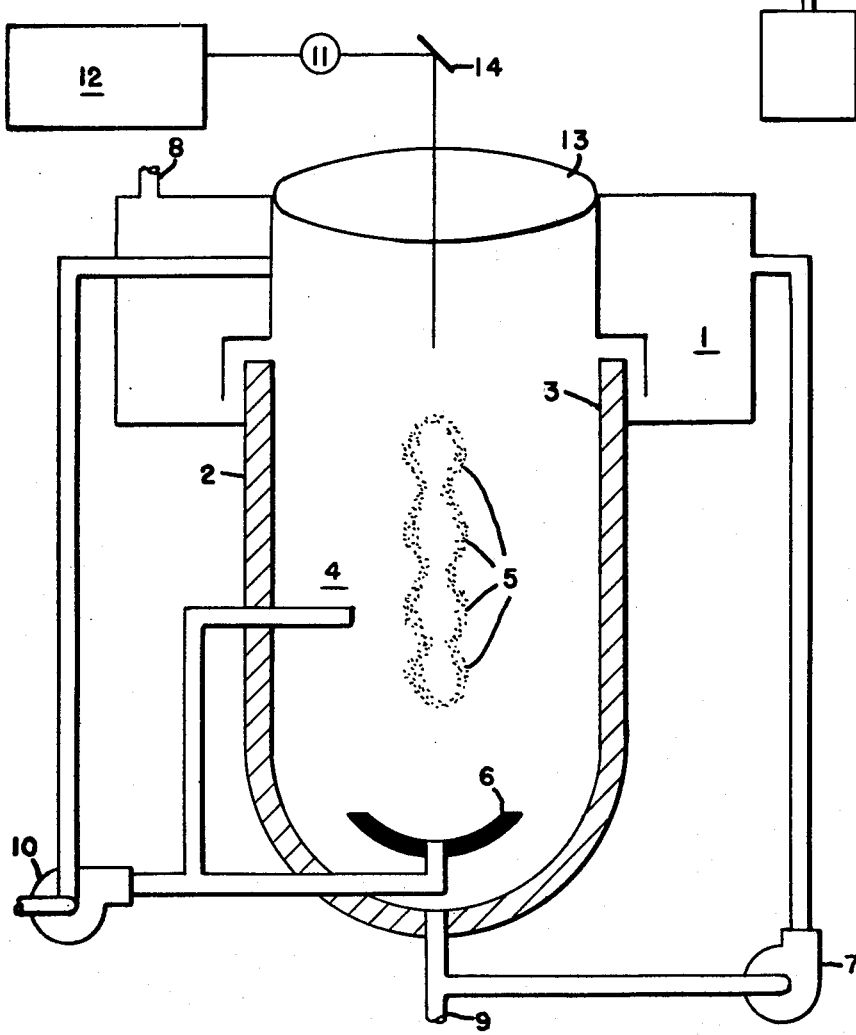

DISINFECTION AND PURIFICATION OF FLUIDS USING FOCUSED LASER RADIATION

BACKGROUND OF THE INVENTION

1. Field of the Invention

This invention relates to a process for purification of contaminated fluids by disinfection and/or reduction in chemical oxygen demand by means of plasmas generated by focused laser radiation.

2. Description of the Prior Art

The disinfection of water and wastewater by the addition of chlorine, calcium hypochlorite or sodium hypochlorite is widely practiced. Disadvantages of chlorine disinfection include undesirable taste and odor properties of the treated water, and the formation of chlorinated organic compounds which have potentially harmful properties when ingested.

An alternative to chlorine in the disinfection of water is ozone, a strong oxidizing agent which not only destroys microorganisms but also oxidizes many organic compounds to innocuous species, e.g. acids which are similar to those found in natural waters.

The use of ozone in conjunction with ultraviolet light, which combination will oxidize certain organic molecules refractory to ozone alone, has been investigated (H. W. Prengle, Jr. et al., *Hydrocarbon Processing*, pp. 82–87, October 1975). The combination of ozone and ultraviolet light also destroys certain inorganic contaminants such as cyanide and ammonia.

Laser plasma is generated by focusing Q modulated laser radiation. The plasma, which resembles an electrical spark discharge, is characterized by high temperatures, escaping electrons which give rise to X-rays, ions produced by ionization of the gaseous medium surrounding the plasma and the possibility of neutrons. Laser plasmas have been produced using a variety of lasers, e.g. $CO_2$ lasers with wavelengths of 9.2–10.6 $\mu$m, Nd:YAG-Nd:glass lasers with wavelengths of 1.06 $\mu$m, ruby lasers with wavelengths of 0.69 $\mu$m at room temperature and iodine lasers with wavelengths of 1.3 $\mu$m. The laser plasma is developed by focusing the energy of the laser radiation into extremely small areas, e.g. a 1 Joule $CO_2$ (10.6 $\mu$m, 1-n sec pulse) laser focused to a diameter of approximately 50 $\mu$m resultes in a power at the focal point of approximately $5 \times 10^{13}$ W/cm$^2$ [R. P. Godwin, *Laser Interaction and Related Plasma Phenomena*, Vol. 3B, H. Schwarz and H. Hura (Eds.), Plenum Press, New York, 1974, pp. 691–711].

When laser plasmas are produced in air or oxygen, ionic and charged molecular oxygen species as well as atomic oxygen and ozone are produced in the plasma. Molecular species such as ozone, which are relatively stable in air or oxygen, escape the plasma and remain present in the surrounding gas. Electronic transitions in oxygen and nitrogen atoms and molecules, present in the plasma, produce ultraviolet emissions during subsequent electronic relaxations, particularly in the cooler, outer regions of the plasma.

Recently the effects of unfocused laser radiation on biological systems have been investigated [Pratt, George W., Biomed. Phys. Biomater. Sci. Lect. Summer Program, 1971 (Publ. 1972) 301-20, edited by Stanley, H. Eugene MIT, Cambridge, Mass.]. Unfocused $CO_2$ and CO lasers, with radiations in the infrared region, were used to deactivate spores or metal surfaces or spores absorbed in paper substrates. In this particular case, sterilization is accomplished, thermally, by rapidly heating the surface of the metal or substrate with incident infrared laser radiation to sufficiently high temperatures, e.g. 500° C., which accomplishes the sterilization procedure. The unfocused laser radiation does not produce a plasma. Therefore, the plasma components, ozone, ultraviolet light, ions, electrons and X-rays are not used to effect sterilization.

More recently, unfocused laser radiation at a wavelength of 1.06 $\mu$m has been used to inactivate bacteria, e.g. E. coli [J. G. Parker, Water and Sewage Works, Vol. 123, pp. 52–53, May 1976]. In this particular application, the unfocused laser radiation interacts with dissolved oxygen which is excited to the singlet $'\Delta_g$ electronic state. The excited singlet oxygen molecules collide with microorganisms resulting in inactivation. Again, the laser radiation that was used was unfocused and the plasma components, ozone, ultraviolet light, ions, electrons and X-rays, were not utilized in sterilization.

Hoskins U.S. Pat. No. 3,405,045 (Oct. 8, 1968) describes a process for irradiating monomer solutions with laser radiation to form free radicals and thereby initiate polymerization.

SUMMARY OF THE INVENTION

The present invention relates to a process for disinfecting an aqueous fluid contaminated with microorganisms, which comprises contacting said fluid with a gas in which a plasma is generated by focused laser radiation.

A further aspect of the present invention relates to a process for reducing the chemical oxygen demand of a waste-water, which comprises contacting said wastewater with an oxygen-containing gas in which a plasma is generated by focused laser radiation.

BRIEF DESCRIPTION OF THE DRAWINGS

The accompanying drawings comprise FIGS. 1 to 4 depicting alternative modes of carrying out the processes of the invention.

DETAILED DESCRIPTION INCLUSIVE OF PREFERRED EMBODIMENTS

Figure 3:
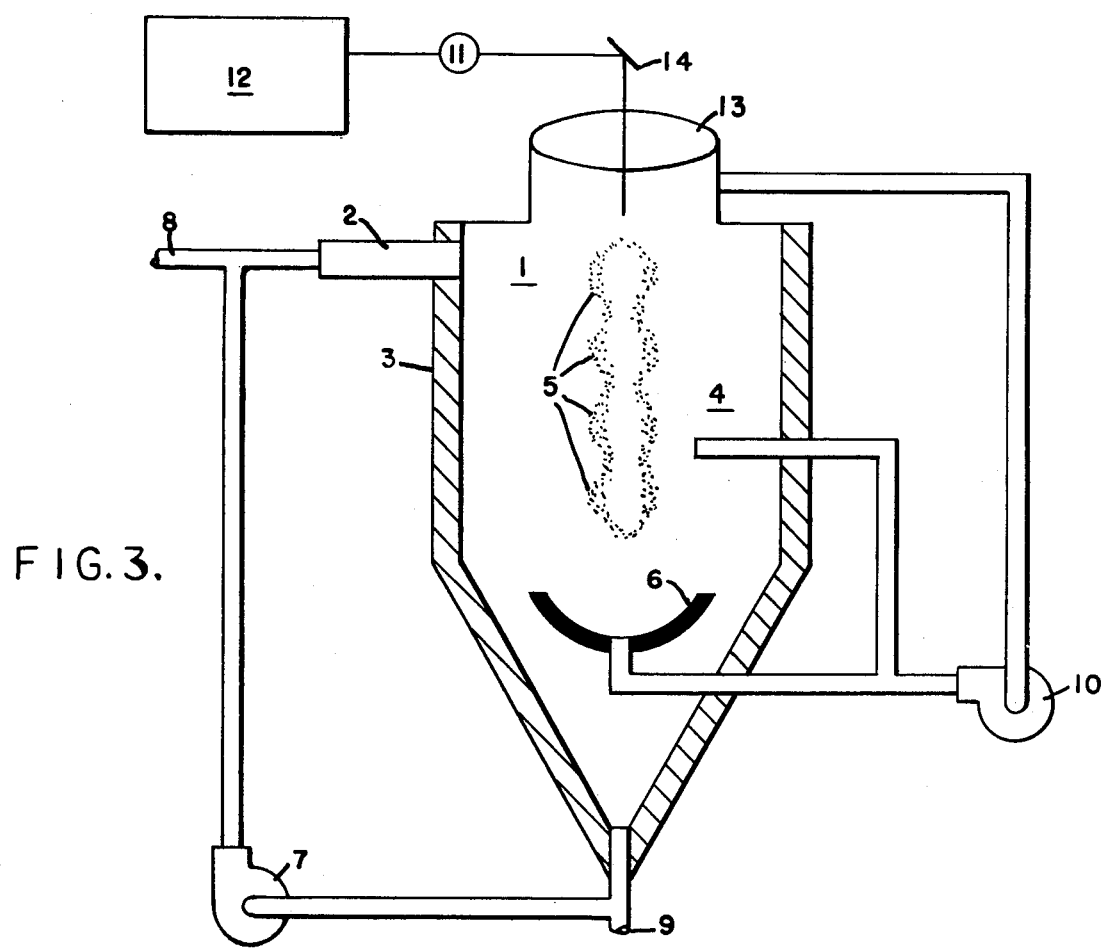

The plasma produced by the focused laser radiation contains ultraviolet light, ions, X-ray, electrons and neutrons, and also contains ozone if the gaseous environment in which the plasma is produced contains oxygen.

The laser radiation that is focused to produce the plasma has a wavelength in the ultraviolet, visible or infrared spectral region, and may, for example, be emitted from a $CO_2$ laser of 9.2–10.6 $\mu$m wavelength, a Nd:YAG or Nd-glass laser of 1.06 $\mu$m wavelength, a ruby laser of 0.69 $\mu$m wavelength, an iodine laser of 1.3 $\mu$m wavelength, a xenon laser with an ultraviolet (1722 Å) wavelength, or a dye laser with a tuneable wavelength. In general for the embodiment of the process, where high power outputs are required, the $CO_2$ laser is preferred.

The laser plasma is generated by focusing the output radiation from the laser. Focusing can be accomplished using a lens of appropriate material, e.g. a germanium lens for focusing $CO_2$ laser radiation. Splitting of the laser radiation into multiple beams, with subsequent focusing of each beam, may be used to generate multiple plasmas from one laser output. For large systems, multiple plasmas or long extended plasmas are preferred.

In the disinfection aspect of the invention, the gaseous environment in which the plasma is produced can comprise any gas or gas mixture not subject to violent reaction in the presence of the radiation. Such gaseous substances include oxygen, nitrogen, argon, helium, neon, carbon dioxide and a mixture of two or more such gases. In the chemical oxygen demand reduction aspect of the invention the gaseous environment must contain oxygen as a source of the ozone needed to oxidize the organic compounds in the wastewater. A preferred gas is therefore an oxygen-containing one containing at least about 21 percent oxygen, such as air, oxygen-enriched air, or pure oxygen. The ozone thus provided serves to simultaneously disinfect the aqueous fluid and to reduce its chemical oxygen demand.

The ozone and ultraviolet light generated by the plasma, together with the high energy particles also produced, are rapidly transferred to the aqueous fluid which is in direct contact with the plasma or in close proximity thereto.

The best mode known to us for carrying out the processes of the invention is described as follows:

An aqueous fluid that is to be disinfected and/or in which the chemical oxygen demand is to be reduced, is contacted with the laser plasma in a reactor. The reactor is designed to facilitate contact of the fluid with the plasma. Referring to FIG. 1, a reactor is shown in which a fluid 1 is rapidly stirred in an enclosed tank 2, using a mixer 3, so that a liquid vortex 4 is created. A gas 5, which will surround the plasma 6, can be injected into the reactor above the fluid, in the fluid, or through the optional plasma reflector 7. The fluid 1 may be recirculated by means of a recirculation pump 8. The fluid may be continually added to the reactor and allowed to overflow or the reactor may be operated on a batch basis. The gas 5 may be continually injected into the reactor or may be recirculated, with a recirculation pump 9, using minimum make-up gas as required. The laser radiation 10, produced by the laser 11, can be directed into a focusing chamber 12 using the required beam guides and deflectors 13. The laser radiation 10 is focused using an appropriate lens 14 to generate the plasma 6 at the lens focal point. An optional reflector 7 may be used to aid the confinement and stability of the plasma. An optional spray system 15 may be used to inject the fluid directly into the plasma.

In a modification depicted in FIG. 2, a reactor 2 is shown in which a fluid 1, which is to be disinfected and/or treated for removal of chemical oxygen demand, is trickled down the walls of the reactor 2 to form a thin liquid film 3. A gas 4 which surrounds the plasma 5, can be injected into the reactor near the plasma or through the optional plasma reflector 6. The fluid 1 may be recirculated by means of a recirculation pump 7. The fluid may be continually added to the reactor at point 8 and withdrawn at point 9 or the reactor may be operated on a batch basis. The gas 4 may be continually injected into and withdrawn from the reactor, or may be recirculated with a recirculation pump 10, using minimum make-up gas as required. The laser radiation 11, produced by the laser 12, can be directed to the focusing lens 13, using the required beam guides and deflectors 14. The focused laser radiation produces a plasma stream along the axis of the reactor. The optional reflector 6 may be used to aid the confinement and stability of the plasma.

In a further modification depicted in FIG. 3, a reactor is shown in which a fluid 1, that is to be disinfected and/or treated for removal of chemical oxygen demand, is tangentially injected at point 2 into the cylindrical body 3 of the reactor, causing a swirling liquid film to form on the walls of the reactor. A gas 4 which surrounds the plasma 5, can be injected into the reactor near the plasma or through the optional plasma reflector 6. The fluid 1 may be recirculated by means of a recirculation pump 7. The fluid may be continually added to the reactor at point 8 and withdrawn at point 9, or the reactor may be operated on a batch basis. The gas 4 may be continually injected into and withdrawn from the reactor, or may be recirculated with a recirculation pump 10, using minimum make-up gas as required. The laser radiation 11, produced by the laser 12, can be directed to the focusing lens 13, using the required beam guides and deflectors 14. The focused laser radiation produces a plasma stream along the axis of the reactor. The optional reflector 6 may be used to aid the confinement and stability of the plasma.

Figure 4:
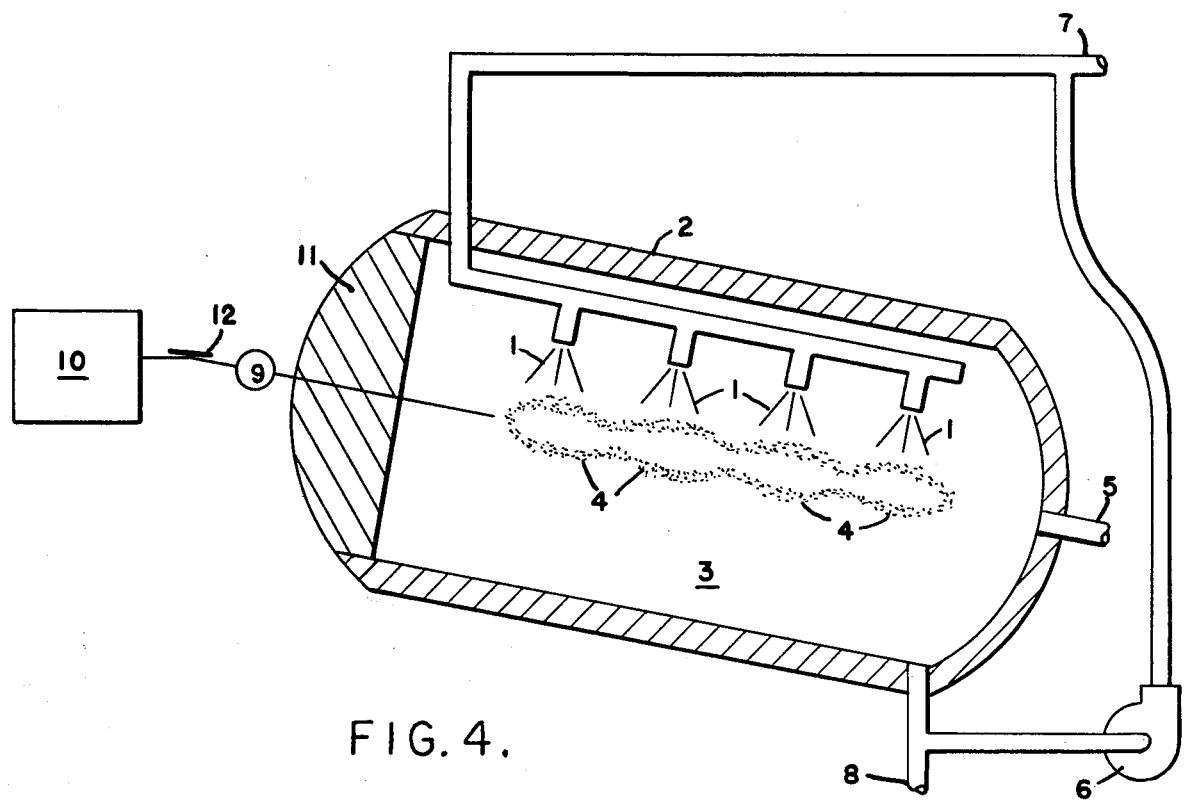

In a further modification depicted in FIG. 4, a reactor is shown in which a fluid 1, that is to be sterilized and/or treated for removal of chemical oxygen demand, is sprayed into a plasma that is contained within an enclosed chamber 2. A gas 3, which surrounds the plasma 4, can be injected into the reactor through the rear reflector at a point 5. The fluid 1 may be recirculated by means of a recirculation pump 6. The fluid may be continually added to the reactor at point 7 and withdrawn at point 8 or the reactor may be operated on a batch basis. The gas 3 may be continually injected into and withdrawn from the reactor, or may be stationary with minimum make-up gas added as required. The laser radiation 9, produced by the laser 10, can be directed to the focusing lens 11, using the required beam guides and deflectors 12. The focused laser radiation produces a plasma stream along the axis of the reactor. The back of the reactor may be curved spherically or elliptically to act as a reflector which aids in the confinement and stabilization of the plasma.

In each of the above fluid-plasma contact reactors, a metal reflector may be situated along the center of the plasma stream axis to reflect the incident plasma beam and thereby aid in the stabilization and confinement of the plasma. Metal reflectors may be fabricated, coated or plated with a variety of metals including copper, aluminum, chromium and stainless steel.

In order to more fully illustrate the nature of the invention and the manner of practicing the same, the following examples are presented.

EXAMPLE 1

A small stirred reactor similar to that in FIG. 1, having an inside diameter of 5.5 inches and a side wall depth of 7 inches, fabricated from acrylic resin, was filled with 2.0 liters of distilled water. Stirring was accomplished using a magnetic stirrer with a 3-inch magnetic stirring bar which contained a brass collar to which a 1-inch diameter parabolic reflector, which was copper coated, was attached. The stirring bar was rapidly turned, by means of an external magnetic stirring unit, to create a liquid vortex. The surface of the reflector stood above the liquid surface at the base of the vortex. Oxygen gas was continually injected into and withdrawn from the vortex air space. A 10.6 $\mu m$ $CO_2$ laser which had a maximum 1 Joule output was used to generate the laser beam. The beam was focused in the vortex of the liquid by means of a germanium lens of 10 cm focal length. When the laser output was pulsed at about 50 pulses (of approximately 0.75J) per second, a plasma occurred in the vortex of the liquid which appeared to be continuous and composed of approximately three streamed nodules, each approximately 1 cm in diameter. The streamed nodules of the plasma were observed in photographs of the plasma. The violet-bluish fluorescence that is characteristic of the presence of ultraviolet light, and is commonly noted around the black light applications, was also observed in the photographs of the plasma.

EXAMPLE 2

The stirred reactor described in Example 1 was charged with 1.5 liters of distilled water and rapidly stirred to create the liquid vortex. The $CO_2$ laser was pulsed at approximately 90 pulses per second. Oxygen was injected into the reactor at a rate of approximately 0.7 liter per minute and was withdrawn, from a point above the plasma, at a rate of approximately 0.64 liter per minute. The withdrawn gases were passed through two midget impingers in series each containing 15 ml of neutral potassium iodide reagent (13.6 g/l $KH_2PO_4$, 26.8 g/l $Na_2HPO_4 \cdot 7H_2O$, and 10.0 g/l KI), which is used to absorb ozone and other iodide oxidizing species. After absorbing the off-gas oxygen stream for 3 minutes, the contents of the impingers, which exhibited a strong iodine color in the first impinger, were analyzed for iodine, using spectrophotometric methods. An iodine equivalent of 59.0 $\mu$g of ozone was detected which is evident of an ozone concentration of 15.6 ppm (Vol/Vol) in the gaseous environment surrounding the plasma.

EXAMPLE 3

The stirred reactor described in Experiment 1 was charged with 1.5 liters of neutral potassium iodide reagent and rapidly stirred to create the liquid vortex. The $CO_2$ laser was pulsed at approximately 50 pulses per second. Oxygen was injected into the reactor at a rate of approximately 0.7 liter per minute. After 3 minutes, the plasma was interrupted. The characteristic iodine color was observed in the liquid and subsequent spectrophotometric analysis revealed a concentration of 0.048 mg/l of ozone in the treated liquid sample.

EXAMPLE 4

Secondary effluent from sewage treatment was steam-sterilized at 120° C., and 1.5 liters of the sterilized effluent was placed into the reactor described in Example 1. The effluent was innoculted with the organism E. coli and rapidly stirred to create the liquid vortex. Oxygen was injected into the reactor at a rate of 0.7 liter per minute. The $CO_2$ laser was pulsed at approximately 50 pulses per second and the focused laser radiation created the plasma in the vortex. Liquid samples were withdrawn from the reactor at times of 0, 15, 30, 45, 60, 75, 90, 105, 120, 240, 480, 960 and 1,020 seconds after generation of the plasma. The liquid samples were analyzed for total bacterial count using the Standard Plate Count (see Standard Methods Water and Wastewater, 13th Edition, 1971) after serial dilution of the samples. The bacterial counts as a function of time, along with the percent survival, are shown in Table 1. The decreasing bacterial counts indicate a continuing disinfection process.

TABLE 1

Bacterial Counts and Survival of E. coli Subjected to Laser Generated Plasma

| Exposure Time, Sec. | Counts/ml | Percent Survival |
|---|---|---|
| 0 | $1.3 \times 10^6$ | 100 |
| 15 | $1.2 \times 10^6$ | 92.3 |
| 30 | $9.0 \times 10^5$ | 69.2 |
| 45 | $7.0 \times 10^5$ | 53.8 |
| 60 | $5.5 \times 10^5$ | 42.3 |
| 75 | $5.0 \times 10^5$ | 38.5 |
| 90 | $3.8 \times 10^5$ | 29.2 |
| 105 | $3.2 \times 10^5$ | 24.6 |
| 120 | $2.5 \times 10^5$ | 19.2 |
| 240 | $9.0 \times 10^4$ | 6.9 |
| 480 | $2.5 \times 10^4$ | 1.9 |
| 960 | $6.0 \times 10^3$ | 0.46 |
| 1,020 | $5.0 \times 10^3$ | 0.38 |

EXAMPLE 5

Secondary effluent from sewage treatment was steam-sterilized at 120° C., and 1.5 liters of the sterilized effluent was placed into the reactor described in Example 1. The effluent was innoculated with the organism E. coli and rapidly stirred to create the liquid vortex. After thoroughly mixing, a sample of the reactor contents was taken. Oxygen was then injected into the reactor at a rate of approximately 0.7 liters per minute. The $CO_2$ laser was pulsed at approximately 100 pulses per second and the focused laser radiation created the plasma in the vortex. The plasma was sustained in the vortex for approximately 850 seconds, after which a sample of the treated reactor contents was taken. Analysis of the samples before and after treatment is as follows:

| | Before Treatment | After Treatment |
|---|---|---|
| Chemical Oxygen Demand, mg/l | 301 | 155 |
| Total Solids, mg/l | 507 | 475 |
| Ash, mg/l | 344 | 341 |
| pH | 8.4 | 8.2 |

The treated sample showed a decrease in the chemical oxygen demand of 48.5 percent which demonstrates the removal of refractory organic substances from the wastewater.

EXAMPLE 6

The stirred reactor described in Example 1 was modified to include a pump and spray system by which the liquid contents of the reactor could be pumped from the bottom of the reactor and recirculated to the top, being discharged through the plasma by means of the spray. The reflector was also changed and a chromium coated reflector was used in this test. The reactor was charged with a dilute aqueous solution of chlorophenol at a concentration of approximately 22 mg/l. The solution was rapidly stirred to create the vortex. Oxygen was injected into the reactor at a rate of approximately 1.0 liter per minute. The $CO_2$ laser was pulsed at approximately 100 pulses per second and the focused laser radiation created the plasma in the liquid vortex. Liquid was continuously recirculated from the bottom of the reactor to the top and sprayed into the plasma at a rate of approximately 0.1 liter per minute. While the solution of chlorophenol was being subjected to the plasma, samples were periodically withdrawn. The samples were analyzed by high pressure liquid chromatographic methods for the chlorophenol content. Chlorophenol concentrations as a function of time are as follows:

| Exposure Time, Min | Concentration, mg/l |
| --- | --- |
| 0 | 22.61 |
| 1 | 21.39 |
| 5 | 21.46 |
| 10 | 20.13 |
| 16 | 19.65 |
| 20 | 19.63 |

The analyzed samples showed a continuing reduction of the highly refractive and toxic chlorophenol compound as a function of time.

We claim:

1. A process for disinfecting an aqueous fluid contaminated with microorganisms, which comprises contacting said fluid with a gas selected from the group consisting of oxygen, nitrogen, argon, helium, neon, carbon dioxide, and a mixture of two or more of said gases in which a continuous plasma is generated by multiple pulses of focused laser radiation said plasma containing ultraviolet light, ions, X-ray, electrons and neutrons, and rapidly transferring said plasma to said aqueous fluid for a time sufficient to disinfect said aqueous fluid.

2. A process according to claim 1 wherein the gas is an oxygen-containing gas.

3. A process according to claim 2 wherein the laser radiation is obtained from a $CO_2$ laser of 9.2–10.6 $\mu$m wavelength.

4. A process according to claim 1 wherein the laser radiation, before focusing, has a wavelength in the ultraviolet, visible, or infrared spectral region.

5. A process according to claim 1 in which the plasma is generated in a vortex produced by rapidly stirring the fluid in an enclosed reactor.

6. A process according to claim 1 which is carried out in an enclosed reactor, and in which the fluid is allowed to trickle by gravity down the side walls of said reactor.

7. A process according to claim 1 which is carried out in a cylindrical reactor into which the fluid is tangentially injected so as to cause a swirling thin film of said fluid on the reactor walls.

8. A process according to claim 1 which is carried out in an enclosed reactor into which reactor the fluid is sprayed so as to pass through the plasma.

9. A process for reducing the chemical oxygen demand of a wastewater, which comprises contacting said wastewater with an oxygen-containing gas in which a continuous plasma is generated by multiple pulses of focused laser radiation said plasma containing ultraviolet light, ions, x-ray, electrons, neutrons, and ozone, and rapidly transferring said plasma to said waste-water for a time sufficient to reduce said chemical oxygen demand.

10. A process according to claim 9 in which the chemical oxygen demand is due to the presence of organic substances resistant to biological degradation.

11. A process according to claim 10 in which the organic substances are halogenated compounds.

12. A process according to claim 9 wherein the laser radiation, before focusing, has a wavelength in the ultraviolet, visible, or infrared spectral region.

13. A process according to claim 9 wherein the laser radiation is obtained from a $CO_2$ laser of 9.2–10.6 $\mu$m wavelength.

14. A process according to claim 9 in which the plasma is generated in a vortex produced by rapidly stirring the fluid in an enclosed reactor.

15. A process according to claim 9 which is carried out in an enclosed reactor, and in which the fluid is allowed to trickle by gravity down the side walls of said reactor.

16. A process according to claim 9 which is carried out in a cylindrical reactor into which the fluid is tangentially injected so as to cause a swirling thin film of said fluid on the reactor walls.

17. A process according to claim 9 which is carried out in an enclosed reactor into which reactor the fluid is sprayed so as to pass through the plasma.

* * * * *